US009460886B2

(12) United States Patent
Jiang et al.

(10) Patent No.: US 9,460,886 B2
(45) Date of Patent: Oct. 4, 2016

(54) HIGH RESOLUTION HIGH QUANTUM EFFICIENCY ELECTRON BOMBARDED CCD OR CMOS IMAGING SENSOR

(71) Applicant: KLA-Tencor Corporation, Milpitas, CA (US)

(72) Inventors: Ximan Jiang, San Mateo, CA (US); Stephen Biellak, Sunnyvale, CA (US); John Fielden, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 79 days.

(21) Appl. No.: 14/614,088

(22) Filed: Feb. 4, 2015

(65) Prior Publication Data

US 2016/0027605 A1 Jan. 28, 2016

Related U.S. Application Data

(60) Provisional application No. 62/027,679, filed on Jul. 22, 2014.

(51) Int. Cl.
*H01J 40/14* (2006.01)
*H01J 31/26* (2006.01)
(Continued)

(52) U.S. Cl.
CPC .............. *H01J 31/26* (2013.01); *G01N 21/88* (2013.01); *H01J 29/46* (2013.01)

(58) Field of Classification Search
CPC ......... G01N 21/88; H01J 29/46; H01J 31/26
USPC ........... 250/207, 214 VT; 313/524, 529, 530
See application file for complete search history.

(56) References Cited

U.S. PATENT DOCUMENTS

| 5,321,334 | A | | 6/1994 | Kinoshita et al. |
| 5,475,227 | A | * | 12/1995 | LaRue ............... G01N 23/2273 250/207 |
| 6,198,221 | B1 | | 3/2001 | Suyama et al. |

(Continued)

OTHER PUBLICATIONS

Grubisic, D., et al., "New Silicon Reach-Through Avalanche Photodiodes with Enhanced Sensitivity in the DUV/UV Wavelength Range", MIPRO 2013, May 20-24, 2013, Opatija, Croatia, pp. 48-54.

(Continued)

*Primary Examiner* — Kevin Pyo
(74) *Attorney, Agent, or Firm* — Bever, Hoffman & Harms, LLP

(57) ABSTRACT

An electron-bombarded detector for detecting low light signals includes a vacuum tube structure defining a cylindrical vacuum tube chamber, a photocathode disposed at a first end of the vacuum tube chamber, a sensor disposed at a second end of the vacuum tube chamber, ring electrodes disposed in the vacuum tube chamber for generating an electric field that accelerates emitted photoelectrons toward the sensor, and a magnetic field generator configured to generate a symmetric magnetic field that applies a focusing lens effect on the photoelectrons. The ring electrodes and magnetic field generator are operating using one of a reduced distance focusing approach and an acceleration/deceleration approach such that the photoelectrons have a landing energy below 2 keV. The use of reflective mode photocathodes is enabled using either multi-pole deflector coils, or ring electrodes formed by segmented circular electrode structures. Large angle deflections are achieved using magnetic or electrostatic deflectors.

21 Claims, 10 Drawing Sheets

(51) Int. Cl.
*G01N 21/88* (2006.01)
*H01J 29/46* (2006.01)

(56) References Cited

U.S. PATENT DOCUMENTS

| | | |
|---|---|---|
| 6,285,018 B1 | 9/2001 | Aebi et al. |
| 2001/0017344 A1 | 8/2001 | Aebi |
| 2006/0054778 A1 | 3/2006 | Suhling |
| 2013/0112856 A1 | 5/2013 | Ferenc |
| 2013/0148112 A1 | 6/2013 | Chuang et al. |
| 2013/0264481 A1 | 10/2013 | Chern et al. |
| 2014/0063502 A1 | 3/2014 | Jiang et al. |

OTHER PUBLICATIONS

Ishigami, Yoshihiro et al.; "Development of a high-sensitivity UV photocathode using GaN film that works in transmission mode", Proceedings of SPIE vol. 8359 in 2012, 10 pages.

Opal, Chet B.; "Evaluation of large format electron bombarded virtual phase CCDs as ultraviolet imaging detectors", SPIE vol. 1158 Ultraviolet Technology III (1989), 8 pages.

Buontempo, S,. "The Megapixel EBCCD: A high-resolution imaging tube sensitive to single photons", Nuclear Instruments & Methods In Physics Research A, Aug. 1998, pp. 255-262.

\* cited by examiner

HIGH RESOLUTION HIGH QUANTUM EFFICIENCY ELECTRON BOMBARDED CCD OR CMOS IMAGING SENSOR

RELATED APPLICATIONS OF THE INVENTION

The present application claims priority to U.S. Provisional Application Ser. No. 62/027,679, entitled HIGH RESOLUTION HIGH QUANTUM EFFICIENCY ELECTRON BOMBARDED CCD OR CMOS IMAGING SENSOR, By Ximan Jiang et al., filed Jul. 22, 2014, and is hereby incorporated by reference in its entirety.

FIELD OF THE INVENTION

This invention relates to the field of optical devices and more particularly to electron bombarded imaging sensors.

BACKGROUND OF THE INVENTION

An image intensifier tube is a vacuum tube device that increases the intensity of available light in an optical system to facilitate visual imaging of low-light processes, such as fluorescence of materials in x-rays or gamma rays (x-ray image intensifier), or for conversion of non-visible light sources, such as near-infrared or short wave infrared to visible.

Image intensifiers based on micro-channel plate (MCP) and proximity focus concept can provide high gain due to MCP magnification, low distortion, and uniform resolution across an entire field of view. However, MCP-based image intensifiers tend to have relatively bad resolution for many critical applications. In addition, MCP may block as much as 40% of the photoelectrons right after the photocathode. Thus, detective quantum efficiency for MCP-based image intensifiers is usually low.

To achieve higher detective quantum efficiency, intensifier tubes based on electrostatic focusing lens or combined magnetic-electrostatic focusing optics may be utilized. Such image intensifier tubes usually have much better detector quantum efficiency (DQE) and resolution than MCP-based image intensifiers. However, electron and photon scattering in the amorphous phosphor scintillating layer can still degrade the final resolution. In addition, fiber plate or relay optical lens is required to transfer the light emitted on the phosphor screen to the final imaging device, such as CCD or CMOS. Resolution and gain can be further degraded at this coupling stage. To collect as much light as possible, high numerical aperture (NA) relay lens may be required. High NA and large field of view (FOV) optics require a relay lens with a large diameter and long profile. The cost of such relay optics may become significant. The shallow depth of focus in such a collection scheme is another concern. All these shortcomings increase the challenges of optical alignment and field service.

To overcome these issues in intensifier based detectors, pixelated image sensors such as CCD or CMOS sensors are placed on the phosphor screen location to directly collect photoelectrons emitted from the photocathode. These kinds of detectors are typically referred to as electron bombarded CCD (EBCCD) detectors or electron bombarded CMOS (EBCMOS) detectors. EBCCD or EBCMOS devices eliminate the electron-to-photon conversion step in phosphor screen and the expensive coupling device between phosphor and CCD or CMOS sensor.

Most current EBCCD/EBCMOS detectors are designed based on proximity focus method to simplify the design, reduce the power requirements and make the detector compact. Proximity focus EBCCD/EBCMOS are disclosed, for example, in U.S. Pat. No. 5,321,334 issued on Jun. 14, 1994 to Katsuyuki Kinoshita and Yoshinori Inagaki, and in U.S. Pat. No. 6,285,018 issued on Sep. 4, 2001 to Verle W. Aebi et al.

A conceptual drawing of proximity-focus EBCCD is shown in FIG. 1. A photocathode layer 101 is coated on a glass substrate 100. A CCD/CMOS chip 104 is placed on a package substrate 105 facing photocathode 101. The whole package is sealed by potting material 103 to form a vacuum tight tube. Photocathode in traditional EBCCD/EBCMOS device is usually in the form of transmission mode. It means incoming photons will pass through the glass window and illuminate the photocathode layer on the side with interface layer to the glass substrate. Upon the incoming photon illumination, photoelectrons 102 are emitted from the vacuum side surface of the photocathode layer, then they will be accelerated by the bias voltage 106 applied between the photocathode layer and the sensor surface.

When photoelectrons are emitted from the photocathode, their initial velocity usually has component normal to the photocathode plane and component parallel to the photocathode plane. The velocity component parallel to the photocathode plane will create lateral spread of the electron cloud originated from the same spot on the photocathode plane. The extent of the lateral spread is proportional to the initial lateral velocity and the traveling time between the photocathode and the CCD/CMOS sensor. To reduce the lateral spread, it is important to reduce the initial lateral speed and reduce the traveling time. Initial lateral speed is determined by the incoming photon energy, photocathode work function and the band gap structure. Traveling time between the photocathode and the sensor is determined by the gap and the accelerating voltage between them. A narrower gap and higher accelerating bias voltage will result in shorter travel time, thus better resolution. However, narrower gap and higher bias voltage means higher electric field strength between the photocathode and the sensor. If the electric field strength approaches 2~4 kV/mm, the risk of arcing increases significantly depending on the vacuum pressure, surface smoothness and materials. To get a sub-pixel resolution, the gap needs to be so small that non-flatness of CCD/CMOS chip, especially on the back-thinned sensor becomes significant. Such a non-uniform gap may results in variation of resolution, localized distortion and increased risk of arcing.

If the gap can't be reduced, bias voltage has to be increased to improve resolution. However, higher energy electrons inside sensor will increase the X-ray yield and damage the CCD/CMOS sensor by increasing dark current and hot pixels and reducing gain due to increased defect density. To improve the lifetime of the EBCCD/EBCMOS sensor, it's better to keep the landing energy of the photoelectrons on the CCD/CMOS chip lower than 1 or 2 keV. Therefore, there is a conflicting requirement between improving lifetime and improving resolution on proximity focus EBCCD/EBCMOS. To achieve high gain at low landing electron energy, boron coating instead of oxide coating is applied on back-thinned EBCCD/EBCMOS. Boron coated back-illuminated sensor has been disclosed in U.S. Published Patent Application No. 2013/0264481 published on Oct. 10, 2013 to Jehn-Huar Chen et al.

To improve resolution, electrostatically focused hybrid EBCCD design has been disclosed in U.S. Pat. No. 5,321, 334 issued on Jun. 14, 1994 to Katsuyuki Kinoshita et al and a research paper published in *Nuclear Instruments and Methods A*, issue 2-3, page 255, August 1998 by S. Buontempo et al. However, electrostatic focused vacuum tube usually has poor focus uniformity or non-flat object/image plane and high image distortion. Such shortcomings limit its application in high resolution Time Delay Integration (TDI) imaging sensors. For example, distortion may be rendered as blur in TDI mode imaging sensors.

Another attempt to improve EBCCD/EBCMOS resolution is disclosed in U.S. Pat. Pub. No. 2013/0148112A1 published on Jun. 13, 2013 to Yung-Ho Alex Chuang et al. The disclosed method involves insert a focusing plate with a micro-lens array between the photocathode and the sensor. However, many photoelectrons emitted from the photocathode will likely be blocked by the closed area on the focusing plate. Thus this approach may reduce the detective quantum efficiency (DQE) of the whole EBCCD/EBCMOS.

The overall DQE of an EBCCD/EBCMOS device is mostly determined by the quantum efficiency (QE) of the photocathode. In a transmission-mode photocathode, photons are mostly absorbed on the front side of the photocathode. Then the energetic electrons inside the photocathode layer need to diffuse to the vacuum side of the photocathode before they can escape the energy barrier created by the work function. Momentum of the energetic electrons may be lost during the diffusion process between the two surfaces. In a reflective mode photocathode, photons are absorbed on the vacuum side of the photocathode. Energetic electrons can immediately escape the photocathode close to the same location. Therefore, a reflective mode photocathode usually has significantly higher quantum efficiency.

It is well-known that reflective mode photocathode can achieve more than 50% to 100% higher quantum efficiency (QE) compared with corresponding transmission mode photocathode. For example, a research paper published in Proceedings of SPIE vol. 8359 in 2012 by Yoshihiro Ishigami, et al compared the QE of GaN photocathode in reflective mode and transmission mode. The QE of GaN photocathode for 266 nm photons can be as high as 37% in reflective mode. Yet the QE will be reduced to 17% in transmission mode. It's almost impossible to implement the reflective mode photocathode in traditional proximity-focus EBCCD/EBCMOS without significantly sacrificing resolution by increasing the tube length. A reflective mode oblique magnetic field focused EBCCD/CMOS device had been reported by C. B. Opal and G. R. Carruthers in the Proceedings of SPIE vol. 1158, page 96-103 in 1989 to improve the resolution and quantum efficiency. Such a device has a magnetic field tilted with respect to the accelerating electric field axis. The oblique magnetic field can deflect the photoelectrons off the normal axis and focus them on to the sensor that is not located on the normal axis. The overall device is bulky. Focus aberrations and geometrical distortion in oblique focus design could be too high for many high resolution TDI imaging applications, such as semiconductor defect inspection equipment.

What is needed is an EBCCD/CMOS device that can achieve high spatial resolution, low landing energy, and high gain. Furthermore there is a need for an EBCCD/CMOS device that can achieve these requirements even if the sensor has many tens of microns or about one hundred microns of non-flatness.

SUMMARY OF THE INVENTION

The present invention is directed to electron-bombarded detectors (e.g., EBCCD or EBCMOS detectors) that utilize various novel structures and methodologies to achieve both high resolution electron optics and low landing energies (e.g., 2 keV or below), thereby providing high quality low light imaging and maximizing the operating lifetime of the CMOS or CCD image sensor.

Two basic approaches are used to obtain high resolution electron optics at low landing energy. In each case ring electrodes are utilized to accelerate the photoelectrons as they leave the photocathode, and a magnetic field generator is utilized to generate a focusing lens effect on the photoelectrons as they pass through a vacuum chamber between the photocathode and the sensor. The first approach is to make the distance between the photocathode and the sensor around 10 mm to 20 mm, a distance that is significantly longer than the gap in traditional proximity EBCCD (usually less than 0.5 mm) and significantly shorter than magnetically focused image intensifier with phosphor screen (usually >40 mm), whereby the photoelectrons are accelerated at a relatively low accelerating electric field to generate the desired low landing energy. In this case, an additional magnetic field generated by a solenoid with current of 3 Amps or less or permanent magnets to achieve high resolution electron optics. In the second basic approach, the ring electrodes near the photocathode receive sequentially increasing voltages such that the photoelectrons accelerate to a peak energy within a short distance along vacuum tube chamber, and the ring electrodes near the CCD/CMOS sensor receive sequentially decreasing voltages such that the photoelectrons decelerate from the peak energy to the desired low landing energy.

Both transmission mode embodiments and reflective mode embodiments are disclosed. In some reflective EB detectors, either electric deflection fields or magnetic deflection fields are utilized to deflect the photoelectrons to the off axis sensor. In some embodiments, one or more of the ring electrodes comprises a segmented circular electrode structure including two or more electrically isolated curved sectors, and different voltages are applied on each curved sector to generate a deflective electric field. In other embodiments, a multi-pole deflector coil is disposed between the vacuum tube structure and a permanent magnet or a solenoid, where the multi-pole deflector coil configured to generate a deflective magnetic field. In large angle reflective mode applications, either an electrostatic deflector or a magnetic deflector are utilized to deflect the photoelectrons to an off axis angle larger than about 30 degrees.

The present invention is also directed to a dark-field inspection system including one or more EB (CCD or CMOS) detectors of the type described above, and an optical system that is configured for directing light to a sample being inspected, for collecting scattered light from the sample, and for directing collected light to the EB detector.

BRIEF DESCRIPTION OF THE DRAWINGS

These and other features, aspects and advantages of the present invention will become better understood with regard to the following description, appended claims, and accompanying drawings, where:

DETAILED DESCRIPTION OF THE DRAWINGS

The present invention relates to an improvement in electron-bombarded detectors for low light signal detection. The following description is presented to enable one of ordinary skill in the art to make and use the invention as provided in the context of a particular application and its requirements. Various modifications to the preferred embodiment will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

Figure 1:
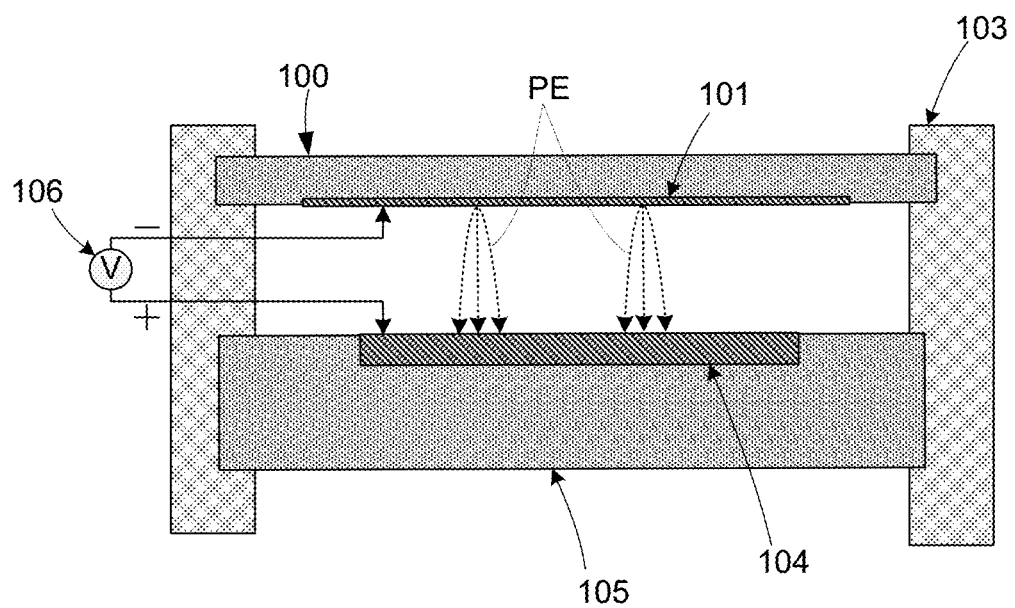
FIG. 1 is a cross-sectional side view showing a traditional proximity-focus EBCCD.
Figure 2:
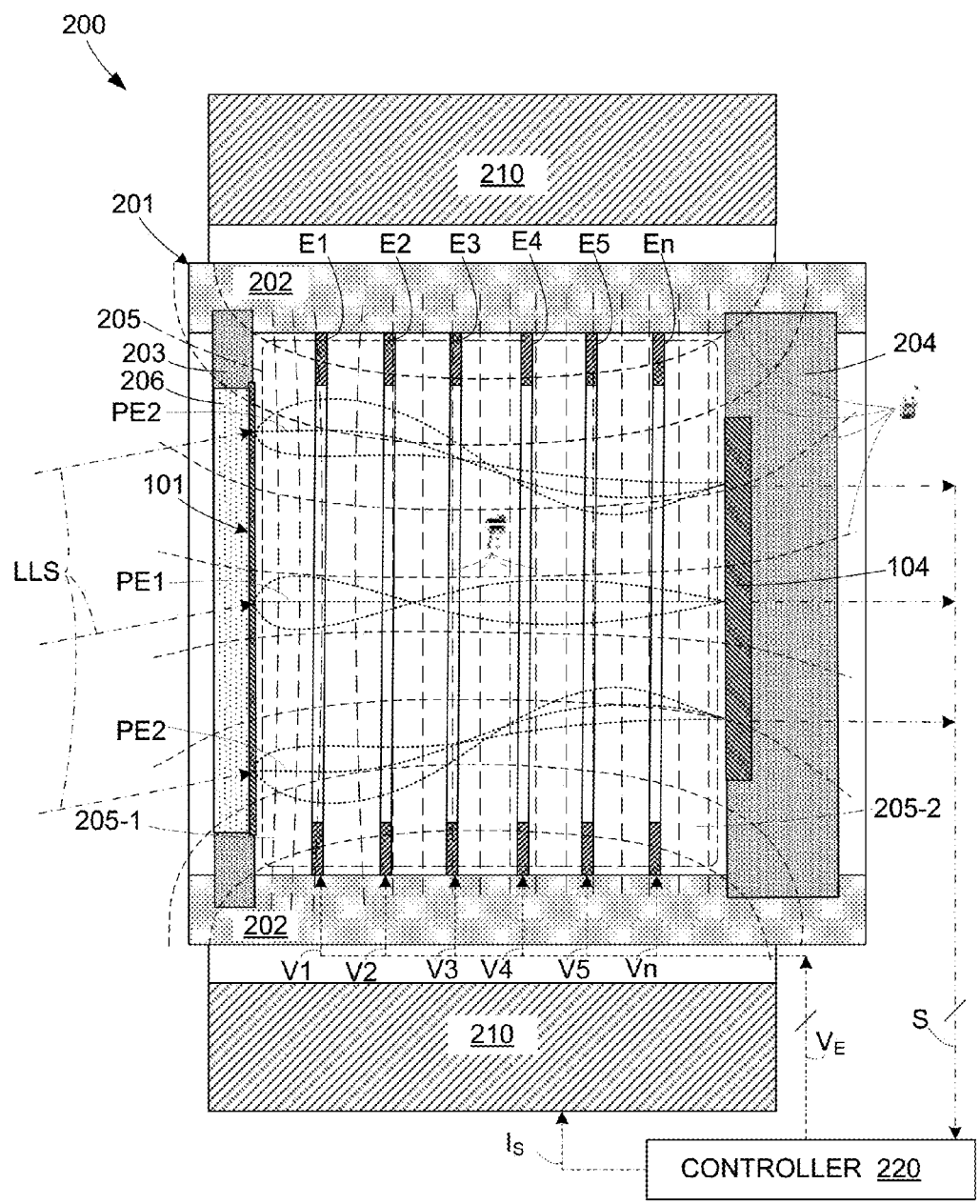
FIG. 2 is a cross-sectional side view showing a transmission mode magnetic focused EBCCD/EBCMOS according to an embodiment of the present invention.

FIG. 2 is a cross-sectional side view showing an electron-bombarded detector (EB-detector) 200, such as an EB-CCD or an EB-CMOS detector, that illustrates an exemplary transmission mode electron-bombarded detector according to an embodiment of the present invention. EB-detector 200 generally includes a vacuum tube structure 201, a photocathode 101, a sensor 104, ring electrodes E1 to En, a magnetic field generator 210 and a controller 220. Vacuum tube structure 201 includes a cylindrical wall 202, a first end wall 203 and a second end wall 204 that collectively form (define) a cylindrical vacuum-tight tube chamber 205 having a circular first end 205-1 and an opposing circular second end 205-2. Cylindrical wall 202, first end wall 203 and a second end wall 204 are constructed using known rigid materials such as ceramic, silicon, glass or plastic. In the transmission mode example of FIG. 2, an illumination window 206 (e.g., glass, optical crystal or clear plastic) is disposed on first end wall 203.

Photocathode 101 and sensor 104 are disposed at opposite ends of vacuum tube chamber 205, with photocathode 101 positioned to generate photoelectrons in response to low light signals (photons), and sensor 104 positioned to capture the emitted photoelectrons after they are accelerated across vacuum tube chamber 205 in the manner described below. Photocathode 101 is disposed on an inside surface of first end wall 203 (i.e., at first end 205-1 of vacuum tube chamber 205) and includes one or more materials that emit photoelectrons in response to said low light signals. In alternative embodiments, photocathode 101 includes one or more alkali based materials, gallium-nitride (GaN), or gallium-arsenide (GaAs), or cesium telluride (CsTe), or a combination including two or more of these materials. Sensor 104 is disposed at second end 205-2 of vacuum tube chamber 205, and is configured to receive at least some of the emitted photoelectrons and to generate an electric signal S in response to the received photoelectrons. In alternative embodiments, sensor 104 is either a charge-coupled device (CCD) image sensor or a CMOS image sensor. In one embodiment, sensor 104 is of a type configured to generate image information using time-delay integration (TDI), such as a TDI CCD, in order to provide higher speed. In one embodiment, sensor 104 is either a back-thinned CMOS or a back-thinned CCD sensor to increase the photon to photoelectron conversion efficiency and thereby improve low-light performance. In yet another embodiment, a boron coating is disposed on a surface of sensor 104 facing towards photocathode 101 to achieve high gain at low landing electron energy and improve the operating lifetime of the sensor. More details on boron coating of sensors can be found in U.S. patent application Ser. No. 13/792,166, filed on Mar. 10, 2013 by Chern et al., and in "Chemical vapor deposition of a-boron layers on silicon for controlled nanometer-deep $p^+$-n junction formation," Sarubbi et al., J. Electron. Material, vol. 39, pp. 162-173, 2010. Both of these documents are incorporated by reference herein.

Ring electrodes E1 to En and magnetic field generator 210 (e.g., a magnetic solenoid, a permanent magnet or both) are configured to accelerate the emitted photoelectrons toward sensor 104, and to focus the accelerated photoelectrons such that they arrive at sensor 104 in a pattern similar to the pattern of their generation. Electrodes E1, E2, E3 . . . En respectively receive voltages V1, V2, V3 . . . Vn from controller 220, thereby generating an acceleration equipotential profile (indicated by generally vertical long-dashed lines) within the EB-detector 200 that accelerates the emitted photoelectrons towards electron sensor 102. Controller 220 is configured to generate and transmit voltages V1, V2, V3 . . . Vn to electrodes E1, E2, E3 . . . En such that the voltages (e.g., V1 and V2) applied on the electrodes adjacent to photocathode 101 (e.g., electrodes E1 and E2) are adjusted to compensate the electron optics aberrations, for example, by creating a high strength electric field near photocathode 101 followed by a relatively low electric field near sensor 104. Such electric field profile creates divergent (negative) lens effect and compensates the positive optics aberrations generated by the magnetic focusing field. Magnetic field generator 210 surrounds vacuum tube structure 201 such that the entire tube structure is immersed in an axially symmetric magnetic field $\vec{B}$ (shown as generally horizontal small-dashed lines in FIG. 2) that is created by the solenoid coil (e.g., in response to solenoid control current $I_S$ generated by controller 220) and/or permanent magnets forming magnetic field generator 210. As indicated in FIG. 2, axially symmetric magnetic field $\vec{B}$ is formed such that both photoelectrons emitted from a location off the tube axis (e.g., photoelectrons PE2 and PE3) and photoelectrons emitted close to the axis (e.g., photoelectron PE1) are brought into focus at the same plane on sensor 104 by adjusting the electric field around photocathode 101 to create a divergent (negative) lens effect to compensate the positive optical aberrations created by the magnetic field.

Referring to the left side of FIG. 2, during operation, low-light signals LLS (i.e., illumination) received through illumination window 206 impinge upon photocathode 101, causing photocathode 101 to emit photoelectrons (e.g., photoelectrons PE1, PE2 and PE3). Once photoelectrons are emitted from the photocathode 101, they are accelerated by electric field $\vec{E}$ generated by electrodes E1, E2, E3 . . . En across the space between the photocathode 101 and solid state sensor 104, and arrive at sensor 104 with a low landing energy while maintaining high resolution electron optics. According to an aspect of the invention, electron-bombarded detector 200 is configured to achieve high resolution electron optics at low landing energy (i.e., such that said photoelectrons arriving at sensor 104 have a landing energy below 2 keV. In contrast, in conventional focused image intensifiers (e.g., such as those disclosed in U.S. Published Patent Application 2014/0063502 A1), the landing energy of the photoelectrons is usually significantly higher than 20 keV to generate enough photons on the scintillator screen. Such a high landing energy can damage CCD or CMOS sensor rapidly in EBCCD/EBCMOS devices.

Figure 3A:
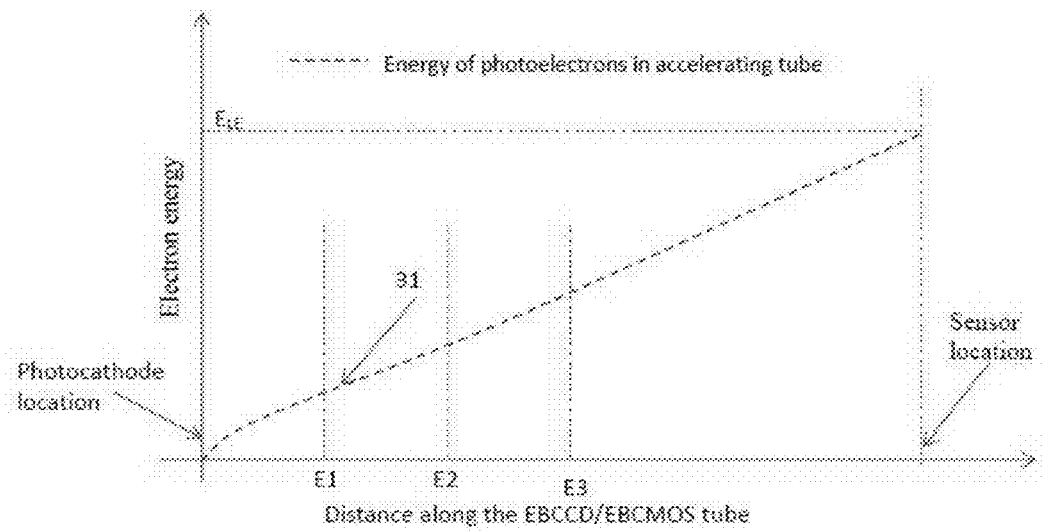
FIG. 3A is an diagram showing energy of photoelectrons along the tube length in an accelerating tube embodiment.

According to alternative embodiments, the present invention utilizes two basic approaches to obtain high resolution electron optics at low landing energy: a reduced distance approach, which is described below with reference to FIGS. 3A and 3B, and an acceleration/deceleration approach, which is described below with reference to FIG. 4.

The reduced distance focusing approach involves reducing the distance between the photocathode plane and the sensor plane while maintaining the accelerating electric field $\vec{E}$ in between such that photoelectrons arrive at the sensor plane having a landing energy of 2 keV or less. As indicated by the graph shown in FIG. 3A, photoelectron energy constantly increases along the flight path between the photocathode plane and the sensor plane. Photoelectrons are accelerated faster and faster until they hit the semiconductor sensor at a landing energy $E_{LE}$. Off axis photoelectrons (e.g., photoelectrons PE2 and PE3, shown in FIG. 2) are accelerated faster than on axis photoelectrons (e.g., photoelectron PE1, FIG. 2) at a location close to the photocathode area.

Figure 3B:
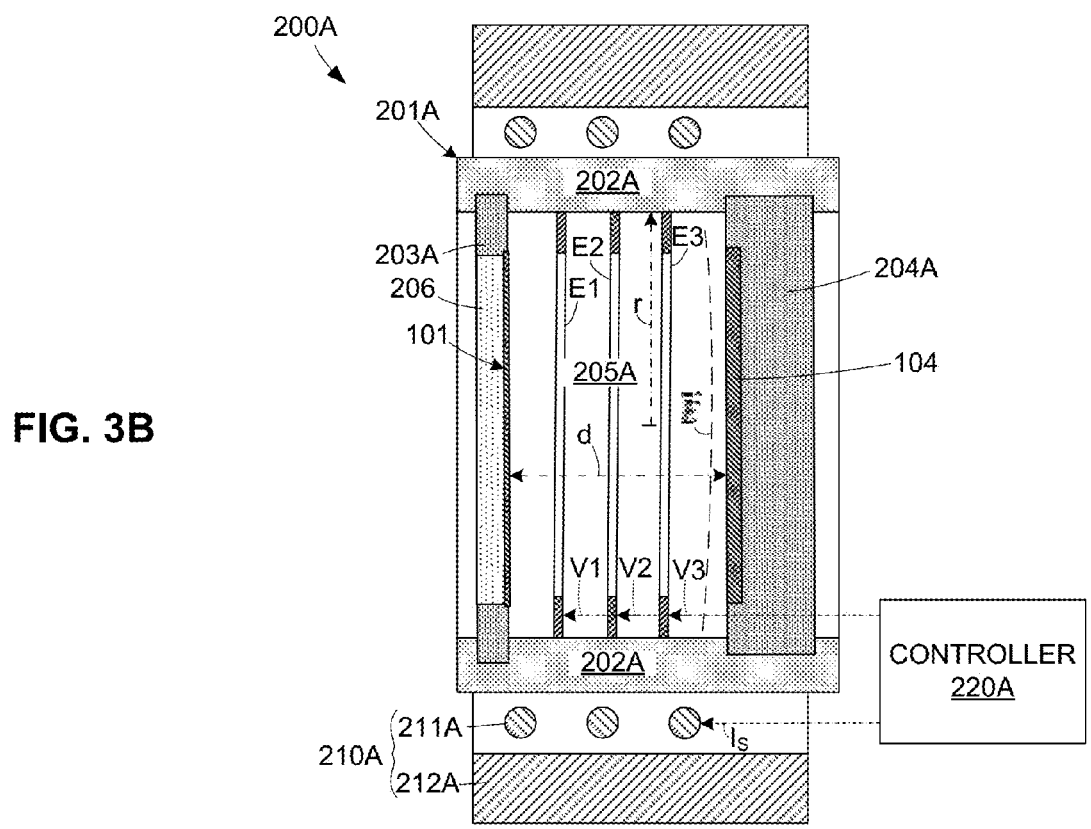
FIG. 3B is a cross-sectional side view showing a transmission mode magnetic focused EBCCD/EBCMOS having a reduced distance configuration according to an embodiment of the present invention

FIG. 3B illustrates an EB detector 200A according to one exemplary implementation of the reduced distance focusing approach, where vacuum tube structure 201A includes a reduced-length cylindrical wall 202A defining a cylindrical tube chamber 205A having a radius r that is larger than a distance d between photocathode 101 and sensor 104. In an exemplary embodiment, radius r is 20 mm, and distance d is 14 mm. Controller 220A applies a current $I_S$ of 2.4 amps to a solenoid 211A of magnetic field generator 210A (which also includes an optional permanent magnet 212A), and also applies suitable bias voltages V1 to V3 to each ring electrode E1 to E3 such that electric field $\vec{E}$ is less than 0.25 kV/mm. In traditional proximity EBCCD/EBCMOS, the gap between the photocathode and the sensor may be less than 0.5 mm, and electric field may need to higher than 2.5 kV/mm to achieve reasonable resolution. Compared with traditional proximity EBCCD/EBCMOS, resolution in this reduced length magnetically focusing EBCCD/EBCMOS tube has been improved by 3× at a gap that is 30 times larger. The electric field in the exemplary device is only 0.086 kV/mm. The risk of arcing is negligible. Compared with traditional proximity EBCCD/EBCMOS, the magnetically focused EBCCD/EBCMOS device disclosed in this application totally eliminates the risk of high voltage arcing and achieves much improved resolution. The depth of focus of such exemplary EBCCD/EBCMOS device can be more than 100 um, which is large enough to handle the non-flatness of many back-thinned EBCCD/EBCMOS device. Non-flatness in back-thinned semiconductor sensor is a serious issue for traditional proximity EBCCD/EBCMOS due to the short gap (<0.5 mm). This reduced distance magnetically focusing approach can compensate the field curvature aberrations on the sensor plane. Final resolution is very sensitive to the electric field strength around the photocathode plane. The higher the electric field strength, the better the resolution. However, short tube length is required to achieve higher electric field strength at the same bias voltage. Short tube length requires higher magnetic focusing field strength. It may increase the diameter of the solenoid or the permanent magnets. In applications with limited space available, a large permanent magnet is not desirable.

Figure 4:
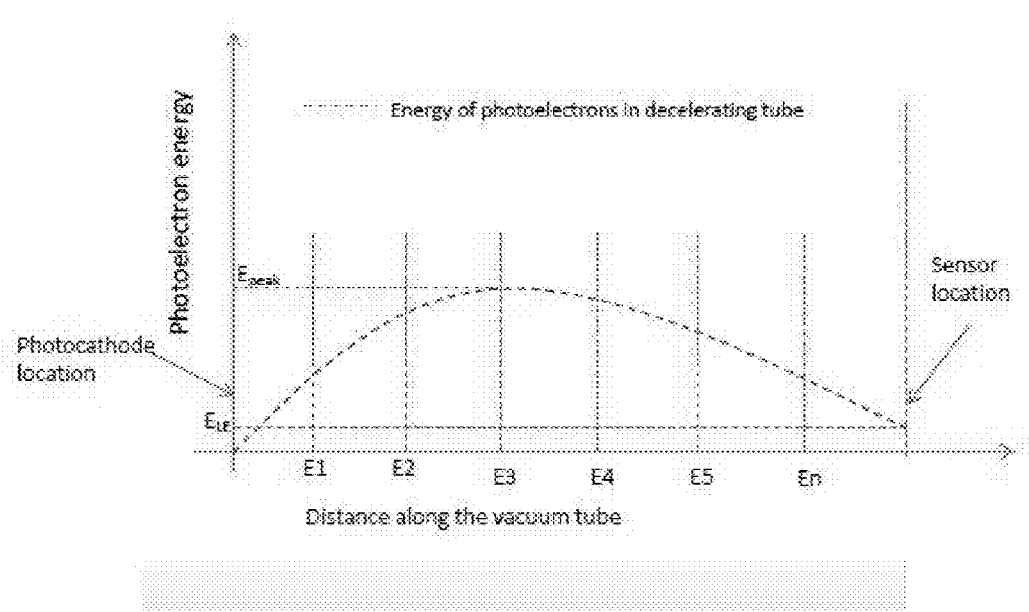
FIG. 4 is a diagram showing energy of photoelectrons along the tube length in a decelerating tube embodiment.

FIG. 4 illustrates exemplary photoelectron energy according to the accelerate/decelerate approach. In this approach, the photoelectrons are accelerated to a peak energy $E_{peak}$ that is substantially higher than the final landing energy $E_{LE}$, then decelerated to final landing energy $E_{LE}$ before arriving at the sensor plane. For example, the photoelectrons are accelerated to peak energy $E_{peak}$, which can be 10 keV or greater, and then decelerated such that their landing energy $E_{LE}$ is 2 keV or lower. In one embodiment of the accelerate/decelerate approach, a high accelerating electric field strength is maintained around the photocathode for better resolution by applying sequentially increasing voltages to a first group of electrodes located adjacent to the photocathode, and a decelerating electric field strength is achieved around the sensor plane by applying sequentially decreasing voltages to a second group of electrodes located adjacent to the sensor. For example, utilizing FIG. 4 for reference, controller 220 is configured to generate voltages V1-V3, which are respectively applied to (first) electrodes E1 to E3, such that V3>V2>V1, whereby photoelectrons are accelerated to a peak energy $E_{peak}$ as depicted in the left half of the graph shown in FIG. 4. Controller 220 is also configured to generate voltages V4, V5 and Vn, which are respectively applied to (second) electrodes E4, E5 and En, such that V4>V5>Vn, whereby photoelectrons are decelerated from peak energy $E_{peak}$ to landing energy $E_{LE}$ at the sensor, as depicted in the right half of the graph shown in FIG. 4. To generate a peak energy of approximately 10 keV, a bias voltage is applied on the photocathode between −200V to −2 kV, the sensor is kept at ground potential, and the bias voltage V3 applied to electrode E3 is equal to or higher than +10 keV. Total tube length from photocathode 101 to sensor 104 in detectors utilizing the accelerate/decelerate approach can be more than twice the length of the corresponding accelerating tube length at the same final photoelectron landing energy and with the same resolution capability. Focus length of the magnetic field in detectors utilizing the accelerate/decelerate approach can be significantly longer than that of the detectors utilizing acceleration-only approaches (e.g., those generating photoelectron energy curves similar to those shown in FIG. 3A). Long focal length can help to reduce the required magnetic field strength, thus reducing the size of the magnetic solenoid and pole pieces.

Although the present invention is described above with specific reference to exemplary EB detectors configured to implement transmission mode photocathodes, the reduced focus distance and acceleration/deceleration approaches of the present invention described above may also be utilized in conjunction with reflective mode photocathodes. As discussed in the background section, EB detectors utilizing reflective mode photocathodes require that the sensor be offset from the optical axis along which light enters the vacuum tube chamber. Because the sensor is offset from photocathode 101B in the reflective mode configuration, a deflection field is needed to deflect the photoelectrons away from the optical (normal) axis to the sensor. To achieve large off-axis deflection within a limited tube length, it's better to apply the deflection force near the photocathode. However, the photocathode area is already immersed in a strong axially symmetric accelerating electric field. To insert additional metal deflector electrodes into the tube vacuum space would create a shielding effect on the field generated by the circular electrodes used to generate the axial electric field, whereby the axial electric field would be perturbed (changed) dramatically, resulting in lower resolution and worse distortion performance.

According to another aspect of the present invention, as set forth in the exemplary embodiments described below with reference to FIGS. 5 to 7, reflective mode EB detectors address the shielding effect issue by utilizing either novel ring electrode structures or a novel magnetic field generator to generate a deflection field without affecting the desired acceleration electric field.

Figure 5:
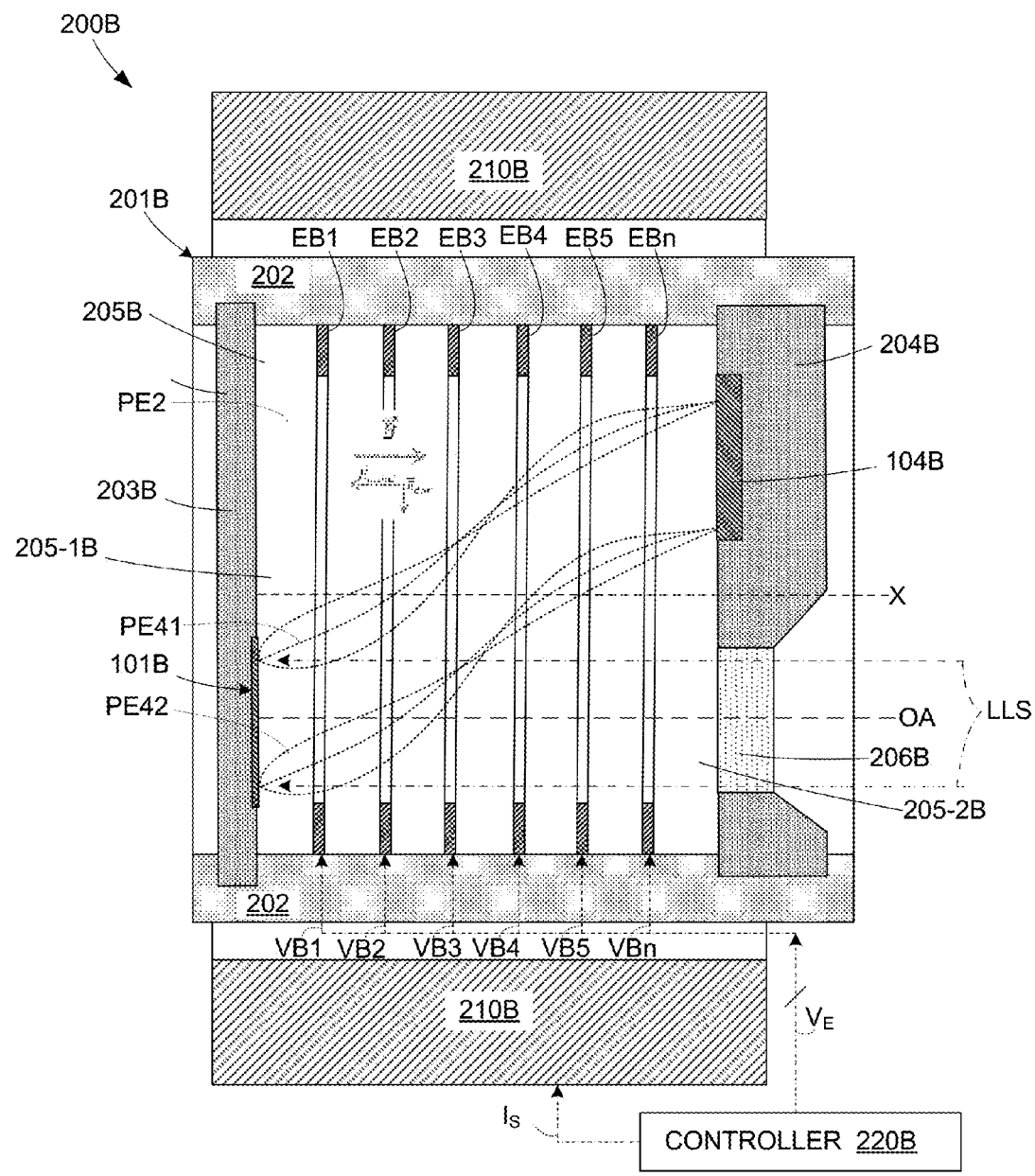
FIG. 5 is a cross-sectional side view showing a reflective mode ECCD/EBCMOS with electrostatic deflection according to another embodiment of the present invention.

FIG. 5 illustrates an exemplary reflective mode EB detector 200B that utilizes ring electrodes EB1 to EBn, each of which is segmented into multiple sectors (see FIGS. 6A and 6B), to generate both a deflective electric field $\vec{E}_{def}$ having sufficient strength to direct photoelectrons to offset sensor 104B, and an axial field $\vec{E}_{axial}$ to accelerate electrons to the desired landing energy when they arrive at sensor 104B. Similar to the transmission mode embodiments described above, EB detector 200B generally includes a vacuum tube structure 201B forming a vacuum-tight tube chamber 205B, a photocathode 101B disposed at a first end 205-1B of chamber 205B, a CCD or CMOS image sensor 104B disposed at a second end 205-1B of chamber 205B, ring electrodes EB1 to EBn disposed inside chamber 205B and coupled to a controller 220B to receive corresponding voltages VB1 to VBn (the voltages applied to the individual sectors of each ring electrode may be individually set or controlled, see FIGS. 6A and 6B and the associated description below), and magnetic field generator 210B that generates a symmetric magnetic field $\vec{B}$.

Vacuum tube structure 201B is similar to structure 201 (see FIG. 2) in that it includes a cylindrical wall 202B, a first end wall 203B and a second end wall 204B that are configured to define cylindrical vacuum-tight tube chamber 205B. Vacuum tube structure 201B differs from structure 201 in that illumination window 206B (e.g., glass, optical crystal or clear plastic) is disposed on second end wall 204B (i.e., at second end 205-2B of chamber 205B) such that light LLS traveling along an optical axis OA is directed through chamber 205B onto reflective mode photocathode 205B, and in that sensor 104B is spaced (offset) from optical axis OA (e.g., on the opposite side of central axis X of cylindrical vacuum-tight tube chamber 205B).

Ring electrodes EB1 to EBn are configured to generate both an axial accelerating electric field (indicated in FIG. 5 by horizontally oriented component $\vec{E}_{axial}$) and a deflection electric field component (indicated in FIG. 5 by vertically oriented component $\vec{E}_{def}$) by applying appropriate voltages to each of the sectors of each of the ring electrodes EB1 to EBn. Deflection component $\vec{E}_{def}$ is generated by the differences between the voltages applied to individual sectors within a single ring electrode. Axial component $\vec{E}_{axial}$ is generated by the differences between the voltages on the sectors of one ring electrode and the voltages on the sectors of the adjacent electrodes. In one embodiment, the voltages applied to the individual sectors of the ring electrodes EB1 to EBn are chosen so as to create an axial component $\vec{E}_{axial}$ that causes photoelectrons to accelerate monotonically as they move from the photocathode 101B towards the sensor 104B in a manner similar to that illustrated in FIG. 3A. In another embodiment, the voltages applied to the individual sectors of the ring electrodes EB1 to EBn are chosen so as to create an axial component $\vec{E}_{axial}$ that causes photoelectrons to accelerate and then decelerate as they move from the photocathode 101B towards the sensor 104B in a manner similar to that illustrated in FIG. 4.

Figure 6A:
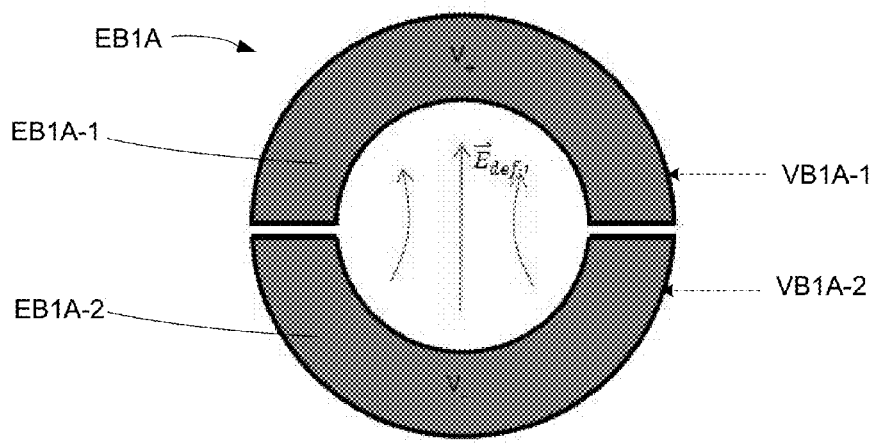
FIG. 6(A) is a top view showing a circular ring electrode divided into two electrodes to act as both a dipole deflector and a ring electrode.
Figure 6B:
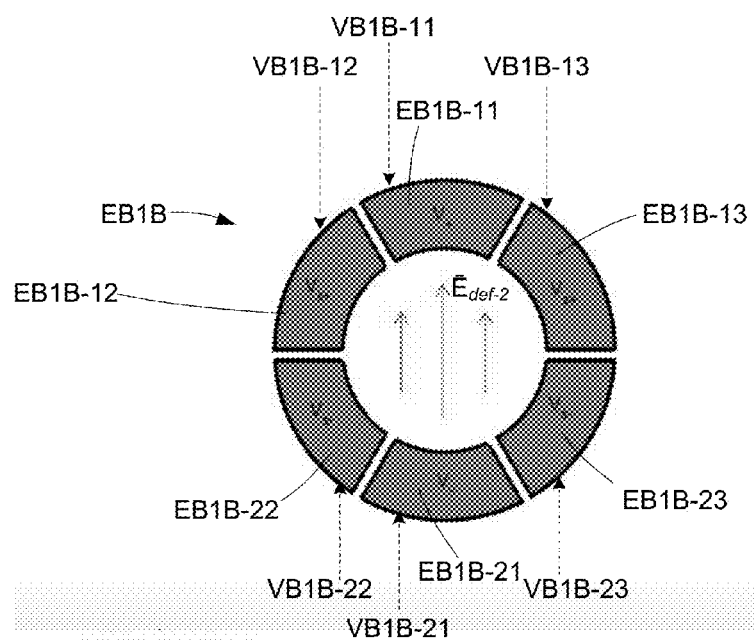
FIG. 6(B) is a top view showing a circular ring electrode divided into six pieces to act as both a sextupole deflector and a ring electrode.

FIGS. 6A and 6B are front views showing segmented circular electrode structures including two or more electrically isolated curved sectors according to exemplary embodiments. FIG. 6A shows ring structure EB1A comprising two semi-circular (curved) sectors EB1A-1 and EB1A-2 that respectively receive voltages VB1A-1 and VB1A-2 during operation. By configuring controller 220B (FIG. 5) to apply different voltages to sectors EB1A-1 and EB1A-2 (e.g., VB1A-1=1500V and VB1A-2=1400V), ring structure EB1A functions as a dipole deflector that produces a deflection electric field component $\vec{E}_{def-1}$, which acts to deflect photoelectrons upward as indicated by the arrows (i.e., toward sensor 104B in FIG. 5). FIG. 6B shows an alternative segmented circular electrode structure EB1B comprising six curved sectors including EB1B-11, EB1B-12 and EB1B-13 forming the upper semi-circular portion, and EB1B-21, EB1B-22 and EB1B-23 forming the lower semi-circular portion. These sectors respectively receive voltages VB1B-11 to VB1B-23 during operation. By applying slightly different voltages to center and side sectors of each semi-circular portion (e.g., applying a more positive voltage VB1B-11 to sector EB1B-11 than voltages VB1B-12 and VB1B-13 applied to sectors EB1B-12 and EB1B-13, which, in turn, are more positive than the voltages VB1B-22 and VB1B-23 applied to sectors EB1B-22 and EB1B-23, which in turn are more positive than the voltage VB1B-21 applied to sector EB1B-21), structure EB1B functions as a sextupole deflector that produces a deflection electric field component $\vec{E}_{def-2}$, which acts to deflect photoelectrons upward as indicated by the arrows (i.e., toward sensor 104B in FIG. 5). By utilizing one or more segmented circular electrode structures in conjunction with the electrode operation described above, the segmented circular electrode structures serve as both deflectors and ring electrodes.

Figure 7:
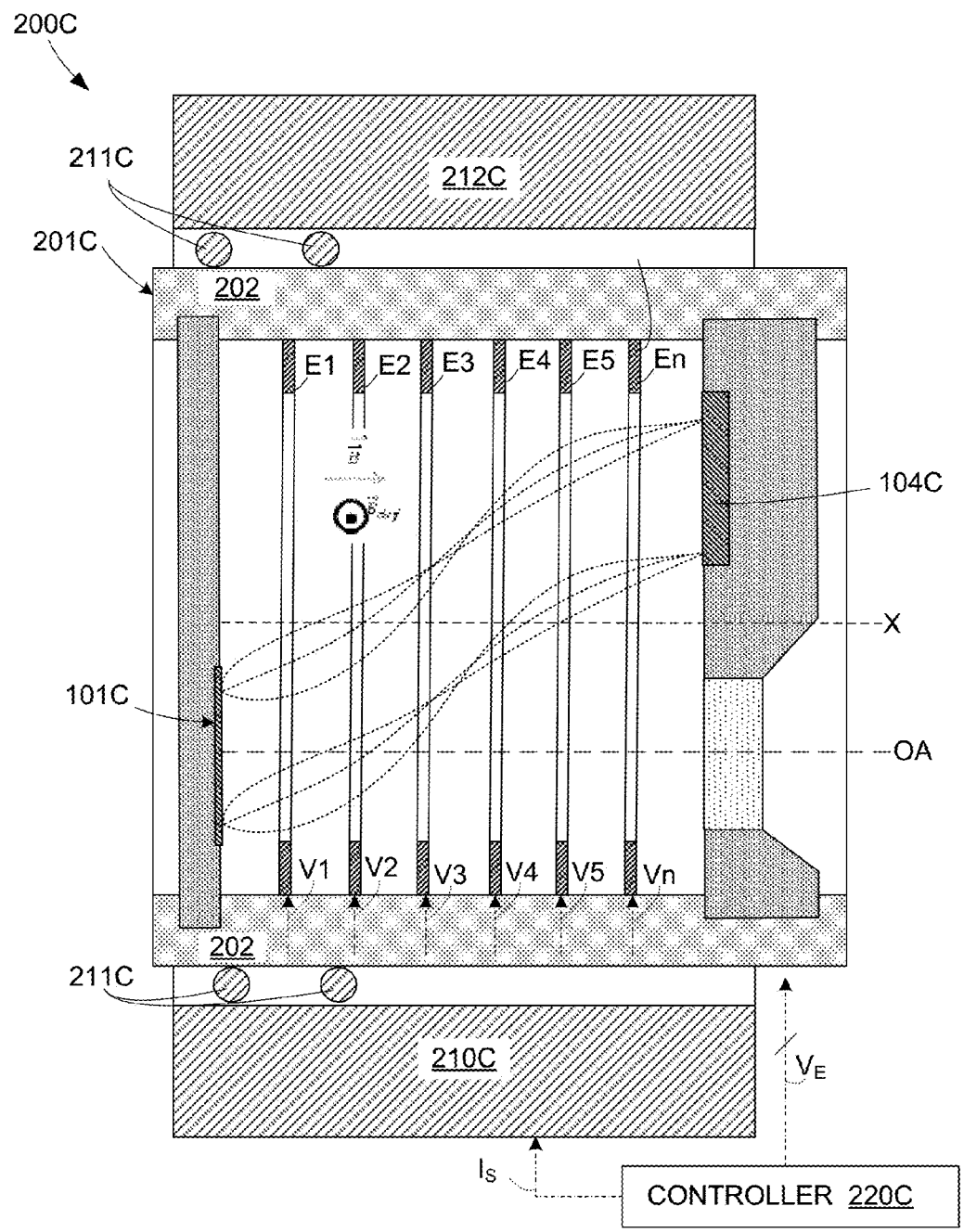
FIG. 7 is a cross-sectional side view showing a ECCD/EBCMOS with a magnetic field deflection according to another embodiment of the present invention.

The reflective mode EB sensors illustrated in FIGS. 5 through 7 are not limited to using ring electrodes divided into two or six equal-area sectors. Variations such as dividing the ring electrodes into sectors of unequal areas, dividing the ring electrodes into four, eight or another number of sectors are all possible alternatives to the exemplary embodiments mentioned above. An advantage of the ring electrode illustrated in FIG. 6B, wherein a circular ring electrode is divided into six pieces to act as both a sextupole deflector and a ring electrode, compared with a dipole design such as that illustrated in FIG. 6A is that deflection field $\vec{E}_{def-2}$ in a sextupole deflector design is more uniform than the deflection field $\vec{E}_{def-1}$ in a dipole deflector design. More uniform deflection field can help to reduce image aberrations such as coma and distortion. One or more of the ring electrodes EB1 to EBn shown in FIG. 5 can be divided into multiple sectors to generate a deflection electric field. The deflection biases on the different sectors can be floated relative to each ring electrode voltage. The different voltages applied to each sector can be generated separately, or a divider resistor chain can be used to generate different bias voltages on different sectors (pole pieces).

FIG. 7 illustrates an exemplary reflective mode EB detector 200C that utilizes a multi-pole magnetic deflector coil 211C disposed between vacuum tube structure 201C and permanent magnet 212C, where multi-pole deflector coil 211C is configured to generate a deflective magnetic field $\vec{B}_{def}$ (directed perpendicular to the drawing sheet) having sufficient strength to direct photoelectrons toward sensor 104C. EB detector 200C also includes a photocathode 101C configured in a manner described above with reference to FIG. 5, and ring electrodes E1 to En that function as described above with reference to FIG. 2. In one embodiment (not shown), multi-pole deflector coils 211C are inserted between vacuum tube structure 201C and a solenoid. Deflector coil 211C is positioned in a manner that generates an out-of-plane magnetic field, whereby photoelectrons leaving photocathode 101C will be deflected upwards toward sensor 104C. Compared with the previous oblique magnet field design, the magnetic solenoid in this design only needs to be slightly larger than the vacuum tube wrapped with deflector coils. The diameter of the magnetic pole piece in our design is significantly smaller. If the magnetic pole piece diameter is smaller, it requires less total magnetic flux to create the same magnetic field on the vacuum tube axis, which in turn can make magnetic solenoid even smaller. The design of the magnetic deflectors is widely known in the field of electron optics. Dipole, quadrupole, sextupole, octopole and other magnetic deflector designs can all be used here.

Figure 8:
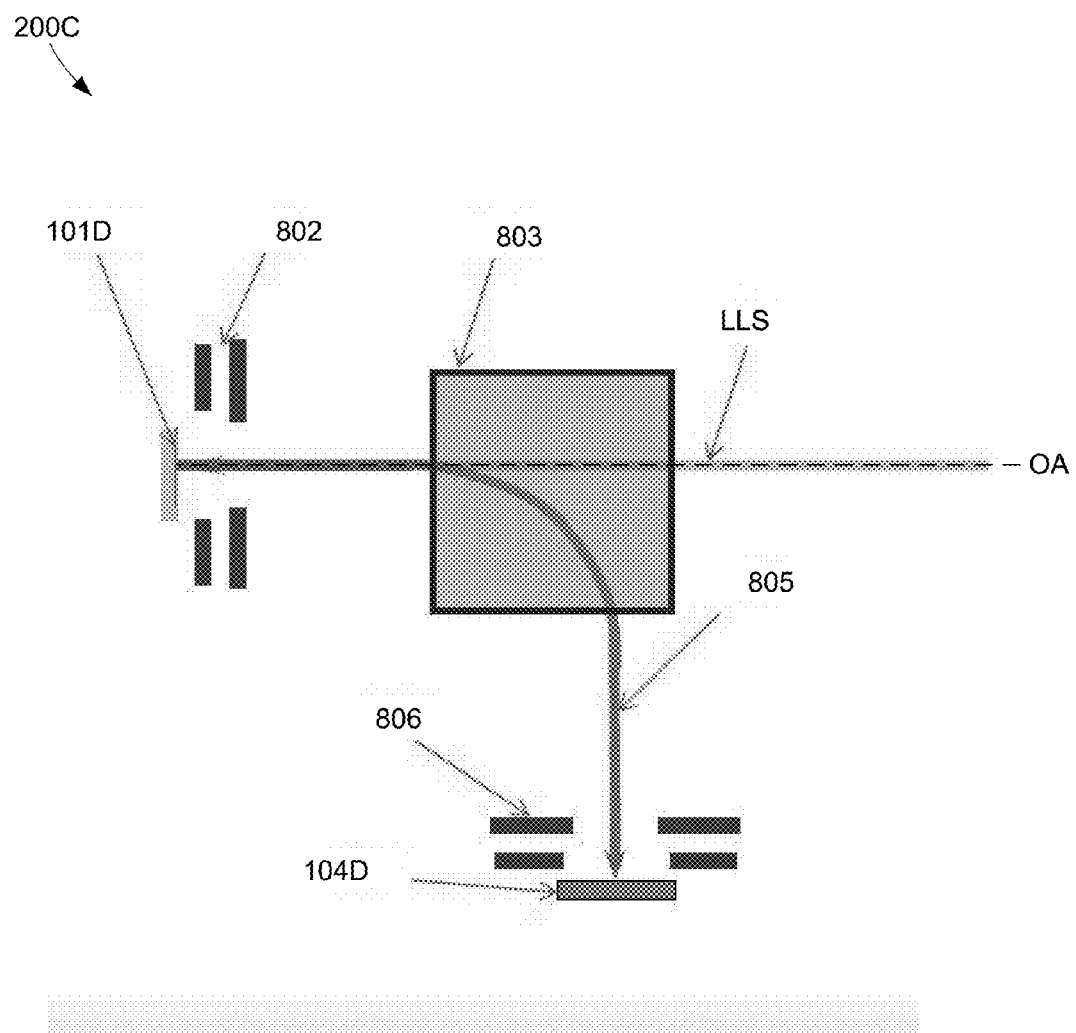
FIG. 8 is a schematic diagram of a large deflection angle reflective mode EBCCD/EBCMOS design.

FIG. 8 illustrates a simplified large deflection angle reflective mode EB detector 200D according to another exemplary embodiment of the present invention. EB detector 200D is utilized, for example, when larger deflection angle is required to provide enough space for camera electronics attached to the sensor. Once photoelectrons 805 are emitted from photocathode 101D under photon illumination LLS, they will be immediately accelerated to a high voltage and focused by electron optics 802. Electron optics 802 may include electrostatic lens and/or magnetic lens (e.g., utilizing ring electrodes E1 to E3 in the manner described above with reference to FIG. 4). Along the path of the photoelectrons 805, a magnetic or electrostatic deflector or sector 803 is used to deflect the photoelectrons to a relatively large angle (e.g., 45° or more) away from the normal (optical) axis to the photocathode 104D. A simple exemplary implementation of magnetic deflector 803 includes two permanent magnet plates with opposite polarity placed close to each other on opposite sides of the photoelectron path. A uniformly strong magnetic deflection field can be formed in the gap. Even though an exemplary deflection angle of 90° is shown in FIG. 8, it is possible to deflect to other angles using the same design. Once the photoelectrons are deflected away from optical axis OA, they will be focused and decelerated by electron optics 806 before they land on the CCD/CMOS sensor 807. Electrostatic and or magnetic lens can be used to form electron optics 806 (e.g., utilizing electrodes E4 to En according to the embodiment described above with reference to FIG. 4). It is possible to have one or more than one intermediate conjugate planes along the path of the photoelectrons.

Figure 9A:
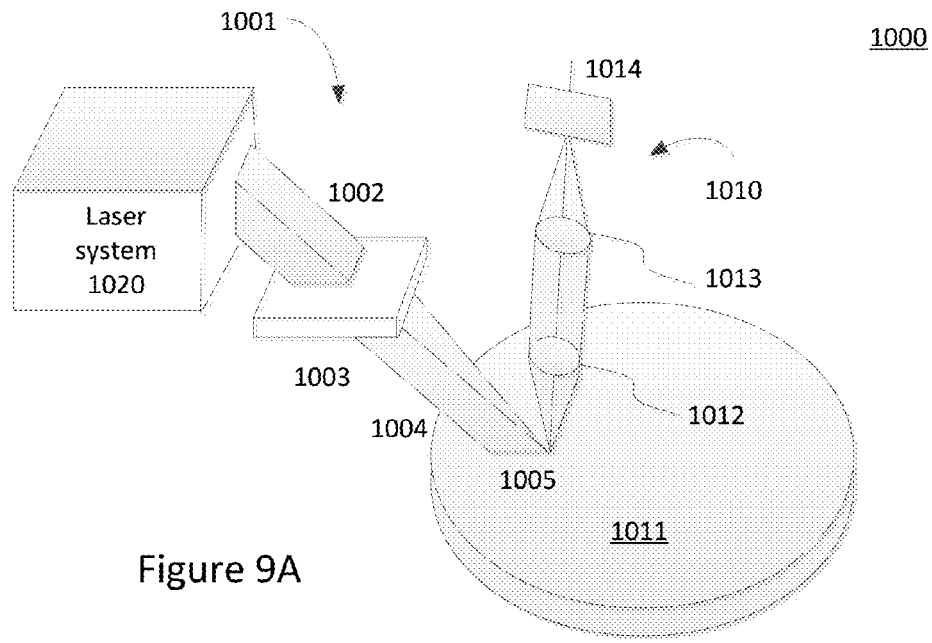
FIGS. 9A and 9B are top-front perspective and side views, respectively, showing surface inspection apparatus including EBCCD/EBCMOS detectors according to yet other embodiments of the present invention.
Figure 9B:
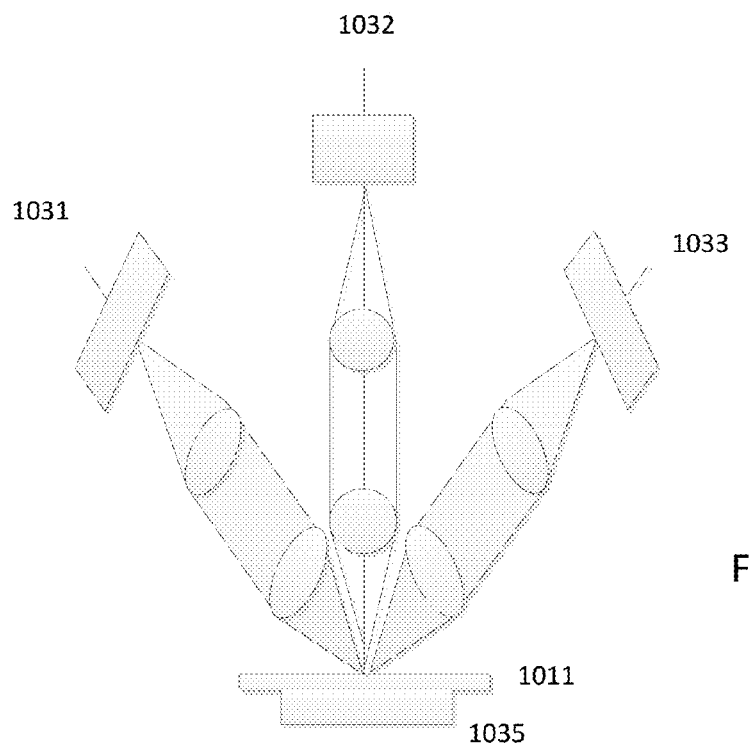

As described in detail below, wafer, reticle and photomask inspection systems can advantageously include a high resolution high QE EBCCD/EBCMOS detector. One embodiment of the exemplary implementation is shown in FIGS. 9A and 9B. FIG. 9A illustrates a surface inspection apparatus 900 that includes illumination system 901 and collection system 910 for inspecting areas of surface 911. As shown in FIG. 9A, a laser system 915 is configured to direct light beam 902 through lens 903. Lens 903 is oriented so that its principal plane is substantially parallel to surface 911 and, as a result, illumination line 905 is formed on surface 911 in the focal plane of lens 903. In addition, light beam 902 and focused beam 904 are directed at a non-orthogonal angle of incidence to surface 911. In particular, light beam 902 and focused beam 904 may be directed at an angle between about 1 degree and about 85 degrees from a normal direction to surface 911. In this manner, illumination line 905 is substantially in the plane of incidence of focused beam 904.

In some embodiments, illumination line might be approximately 1 or 2, or a few, mm long and 1, 2 or a few μm wide. In some embodiments, instead of a line focus, the illumination may be focused into a series of discrete spots.

Collection system 910 includes lens 912 for collecting light scattered from illumination line 905 and lens 913 for focusing the light coming out of lens 912 onto a device, such as an EBCCD detector 914 including the above-described control device. Dynamic adjustment of the gain of EBCCD detector 914 is important in this kind of inspection system because the scattered and diffracted light levels (and the efficiency of the filters) can vary dramatically from one region of a wafer to another due to the different patterns on the wafer.

In one embodiment, EBCCD detector 914 may include a linear array of detectors. In such cases, the linear array of detectors within EBCCD detector 914 can be oriented parallel to illumination line 915. In one embodiment, multiple collection systems can be included, wherein each of the collection systems includes similar components, but differ in orientation. For example, FIG. 9B illustrates an exemplary array of collection systems 921, 922, and 923 for a surface inspection apparatus (wherein its illumination system, e.g. similar to that of illumination system 901, is not shown for simplicity). U.S. Pat. No. 7,525,649, which issued on Apr. 8, 2009 and is incorporated by reference herein, describes certain aspects of inspection system 901 in greater detail.

Figure 10:
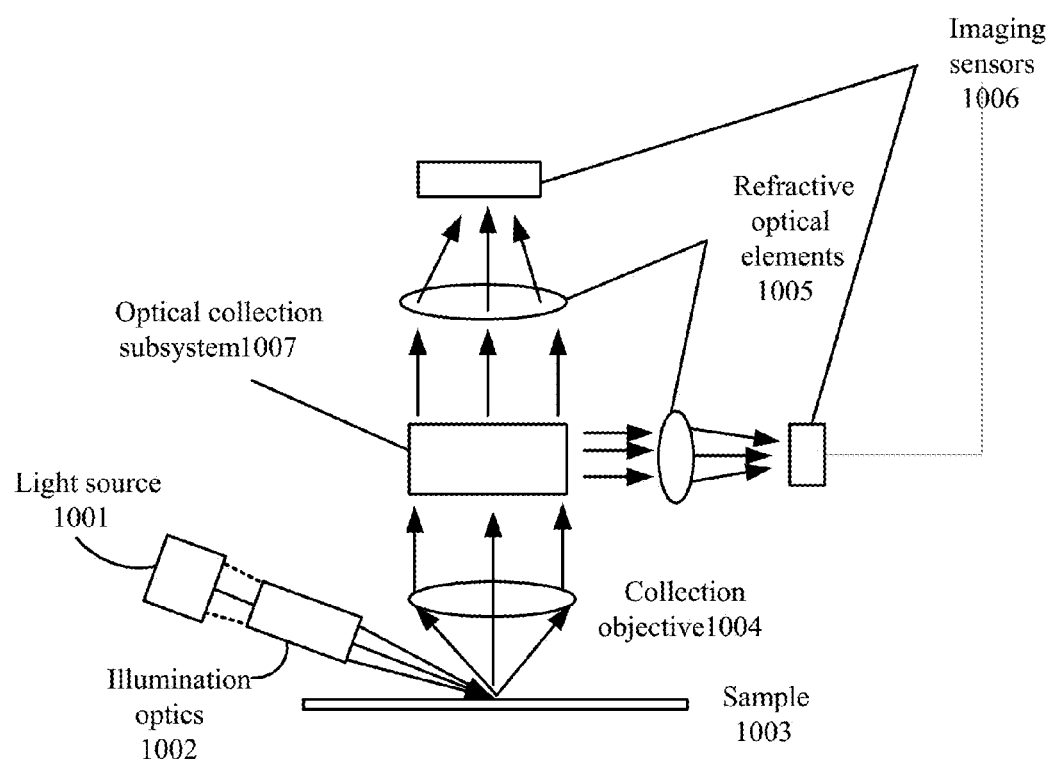
FIG. 10 is a simplified side view showing a dark-field wafer inspection system including a plurality of EBCCD/EBCMOS detectors according to another embodiment of the present invention.

FIG. 10 illustrates another dark-field wafer inspection system 1000 including a plurality of EBCCD/EBCMOS detectors. In system 1000, illumination optics 1002 receives the light beam(s) emitted by a light source 1001. In one embodiment, illumination optics 1002 may include multiple beam splitters and reflective optical elements that provide substantially parallel output light beams to a refractive optical element. That refractive optical element, in turn, can focus the multiple light beams onto a sample 1003.

An optical collection subsystem 1007 including a scattered light collector and other elements, such as one or more apertures, splitters, polarizing elements, and reflective optical elements, can direct the light scattered from sample onto two image detectors 1006. In one embodiment, optical collection subsystem 1007 may further include refractive optical elements 1005 that are configured to assist the other elements of optical collection subsystem 1007 in imaging the scattered light onto image detectors 1006. In one embodiment, at least one of image detectors 1006 can include the above-described EBCCD/EBCMOS detector. For example, in one embodiment, one detector may be optimized for substantial light scattering while another detector may be optimized for substantially low light scattering. Therefore, during some portions of a scan, the optical element may be configured to direct one portion of the scattered light to one image detector optimized for substantial light scattering and to direct another, different portion of the scattered light to a different image detector that is optimized for low-light scattering. U.S. Patent Pub. No. 2014/0009759 A1 issued to Guoheng Zhao et al. in 2014 describes dark field wafer inspection system 900 in more detail.

It is to be understood that the foregoing descriptions are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

The invention claimed is:

1. An electron-bombarded detector for detecting low light signals, said electron-bombarded detector comprising:
   a vacuum tube structure defining a cylindrical vacuum tube chamber having a first end and an opposing second end;
   a photocathode disposed at said first end of the vacuum tube chamber and including a material that emits photoelectrons in response to said low light signals;
   a sensor disposed at the second end of the vacuum tube chamber and configured to receive at least some of said emitted photoelectrons, and to generate an electric signal in response to said received photoelectrons;
   a plurality of ring electrodes disposed in the vacuum tube chamber, each said ring electrode configured to generate, in response to an applied voltage, an electric field that accelerates said emitted photoelectrons toward said second end of the vacuum tight chamber;
   a magnetic field generator disposed adjacent to the vacuum tube structure and configured to generate a symmetric magnetic field in the vacuum tight chamber such that said symmetric magnetic field applies a focusing lens effect on said accelerated photoelectrons; and
   a controller configured to transmit said applied voltages to said plurality of ring electrodes such that the applied voltages on the electrodes around the photocathode are adjusted to compensate the electron optics aberrations,
   wherein said electron-bombarded detector is configured such that said photoelectrons received by said sensor have a landing energy below 2 keV.

2. The electron-bombarded detector according to claim 1, wherein the vacuum tube structure is configured such that a radius of the cylindrical tube chamber is larger than a distance between the photocathode and the sensor,
   wherein the magnetic field generator comprises a solenoid, and
   wherein the controller is further configured to apply a bias current of 3 Amps or less to the solenoid, and configured to apply sequentially increasing voltages to said plurality of ring electrodes such that said electric field is less than 0.1 kV/mm at said sensor.

3. The electron-bombarded detector according to claim 1, wherein the plurality of ring electrodes include two or more first ring electrodes disposed adjacent to said first end of the vacuum tube chamber, and two or more second electrodes disposed adjacent to said second end of the vacuum tube chamber, and
   wherein the controller is further configured to apply sequentially increasing voltages to said first electrodes such that said photoelectrons accelerate to a peak energy within said vacuum tube chamber, said controller also being configured to apply sequentially decreasing voltages to said second electrodes such that said photoelectrons decelerate from said peak energy to said landing energy before arriving at said sensor.

4. The electron-bombarded detector according to claim 1, further comprising a window disposed at the second end such that light traveling on an optical axis is directed onto the photocathode, wherein the sensor is spaced from the optical axis, and wherein at least one of the plurality of ring electrodes and the magnetic field generator is configured to generate a deflection field.

5. The electron-bombarded detector according to claim 4, wherein one or more of the ring electrodes comprises a segmented circular electrode structure including a plurality of electrically isolated curved sectors, and
   wherein the controller is configured to apply a different voltage to each curved sector of the plurality of electrically isolated curved sectors such that said segmented circular electrode structure generates a deflective electric field sufficient to direct photoelectrons toward said sensor.

6. The electron-bombarded detector according to claim 5, wherein said segmented circular electrode structure comprises first and second semicircular sectors, and
   wherein the controller includes means for applying a first voltage to said first semicircular sector and a second voltage to said second semicircular sector such that said segmented circular electrode structure forms a dipole deflector.

7. The electron-bombarded detector according to claim 5, wherein said one or more of said segmented circular electrode structure comprises six or more curved sectors, and
   wherein the controller includes means for applying a different voltage to each of said six or more curved sectors such that said segmented circular electrode structure forms a multipole deflector.

8. The electron-bombarded detector according to claim 4, further comprising a multi-pole deflector coil disposed between the vacuum tube structure and said permanent magnet, said multi-pole deflector coil configured to generate a deflective magnetic field sufficient to direct photoelectrons toward said sensor.

9. The electron-bombarded detector according to claim 4, further comprising one of an electrostatic deflector and a magnetic deflector configured to deflect the photoelectrons by an angle of 30 degrees or more away from said optical axis between said photocathode and said sensor.

10. The electron-bombarded detector of claim 1, wherein said sensor comprises one of a charge-coupled device (CCD) image sensor and a CMOS image sensor.

11. The electron-bombarded detector of claim 1, wherein the sensor is configured to perform time-delay integration.

12. The electron-bombarded detector of claim 1, wherein the sensor comprises one of a back-thinned CMOS and a back-thinned CCD sensor.

13. The electron-bombarded detector of claim 1, wherein the sensor comprises a boron coating on a surface thereof.

14. The electron-bombarded detector of claim 1, where the photocathode comprises at least one of (a) one or more alkali based materials, (b) GaN, (c) GaAs, and (d) CsTe.

15. A method for operating an electron-bombarded detector for detecting low light signals, said electron-bombarded detector including:

a vacuum tube structure defining a cylindrical vacuum tube chamber having a first end and an opposing second end;

a photocathode disposed at said first end of the vacuum tube chamber and including a material that emits photoelectrons in response to said low light signals; and a sensor disposed at the second end of the vacuum tube chamber and configured to receive at least some of said emitted photoelectrons, and to generate an electric signal in response to said received photoelectrons, said method comprising:

applying sequentially increasing voltages to a plurality of first ring electrodes disposed in the vacuum tube chamber and located adjacent to said first end of the vacuum tube chamber, whereby said plurality of first ring electrodes generate an accelerating electric field that causes said emitted photoelectrons to accelerate to a peak energy within said vacuum tube chamber; and applying sequentially decreasing voltages to a plurality of second ring electrodes disposed in the vacuum tube chamber and located adjacent to said second end of the vacuum tube chamber, whereby said plurality of second ring electrodes generate a decelerating electric field that causes said emitted photoelectrons to decelerate from said peak energy to a landing energy before reaching said sensor.

16. The method of claim 15, wherein applying said sequentially increasing voltages comprises increasing an energy of said emitted photoelectrons to above 10 keV, and wherein applying said sequentially increasing voltages comprises decreasing said energy of said emitted photoelectrons to below 2 keV.

17. The method of claim 15, further comprising deflecting the emitted photoelectrons away from a normal axis of the cylindrical vacuum tube chamber before said emitted photoelectrons reach said sensor.

18. The method of claim 17, wherein deflecting the emitted photoelectrons comprises generating a uniform magnetic deflection field using magnetic deflector wrapped around the vacuum tube structure and placed inside a solenoid pole piece.

19. The method of claim 17, wherein the electron-bombarded detector further comprises one or more segmented circular electrode structures disposed in said cylindrical vacuum tube chamber, each said one or more segmented circular electrode structures including a plurality of electrically isolated curved sectors, and wherein deflecting the emitted photoelectrons comprises applying a different bias voltages to each curved sector of each said one or more segmented circular electrode structures.

20. The method of claim 15, further comprising deflecting said emitted photoelectrons by an angle of 30 degrees or more away from an optical axis of the cylindrical vacuum tube chamber after said emitted photoelectrons are accelerated to said peak energy, and before said photoelectrons are decelerated from said peak energy to said landing energy.

21. A dark-field inspection system including:

an electron-bombarded detector; and an optical system configured to direct light to a sample being inspected, and configured to collect scattered light from the sample and to direct the collected light to said electron-bombarded detector, wherein said electron-bombarded detector comprises:

a vacuum tube structure defining a cylindrical vacuum tube chamber having a first end and an opposing second end;

a photocathode disposed at said first end of the vacuum tube chamber and including a material that emits photoelectrons in response to said collected light;

a sensor disposed at the second end of the vacuum tube chamber and configured to receive at least some of said emitted photoelectrons, and to generate an electric signal in response to said received photoelectrons;

a plurality of ring electrodes disposed in the vacuum tube chamber, each said ring electrode configured to generate, in response to an applied voltage, an electric field that accelerates said emitted photoelectrons toward said second end of the vacuum tight chamber;

a magnetic field generator disposed adjacent to the vacuum tube structure and configured to generate a symmetric magnetic field in the vacuum tight chamber such that said symmetric magnetic field applies a focusing lens effect on said accelerated photoelectrons; and a controller configured to transmit said applied voltages to said plurality of ring electrodes such that the applied voltages on the electrodes around the photocathode are adjusted to compensate electron optics aberrations, wherein said electron-bombarded detector is configured such that said photoelectrons received by said sensor have a landing energy below 2 keV.

* * * * *

UNITED STATES PATENT AND TRADEMARK OFFICE
CERTIFICATE OF CORRECTION

PATENT NO. : 9,460,886 B2
APPLICATION NO. : 14/614088
DATED : January 10, 2017
INVENTOR(S) : Ximan Jiang, Stephan Biellak and John Fielden It is certified that error appears in the above-identified patent and that said Letters Patent is hereby corrected as shown below:

In the Specification

Column 3, Line 13, amend "insert" to "inserting"
Column 3, Line 46, amend "EBCCD/CMOS" to "EBCCD/EBCMOS"
Column 3, Line 58, amend "EBCCD/CMOS" to "EBCCD/EBCMOS"
Column 3, Line 60, amend "EBCCD/CMOS" to "EBCCD/EBCMOS"
Column 4, Line 21, add omitted word "is" between the words "field generated"
Column 5, Line 8, amend "ECCD/EBCMOS" to "EBCCD/EBCMOS"
Column 5, Line 16-17, amend "ECCD/EBCMOS" to "EBCCD/EBCMOS"
Column 6, Line 42, amend "102" to "104"
Column 6, Line 48, add omitted word "field" between the words "electric near"
Column 9, Line 36, amend "205-1B" to "205-2B"
Column 9, Line 53, amend "205B" to "201B"
Column 11, Line 60, amend "and or" to "and/or"
Column 12, Line 6, amend "900" to "1000"
Column 12, Line 6, amend "901" to "1001"
Column 12, Line 7, amend "910" to "1010"
Column 12, Line 7, amend "911" to "1011"
Column 12, Line 8, amend "915" to "1015"
Column 12, Line 9, amend "902" to "1002"
Column 12, Line 9, amend the first and second occurrences of "903" to "1003"
Column 12, Line 10, amend "911" to "1011"
Column 12, Line 11, amend "905" to "1005"
Column 12, Line 11, amend "911" to "1011"
Column 12, Line 12, amend "903" to "1003"
Column 12, Line 12, amend "902" to "1002"
Column 12, Line 13, amend "904" to "1004"
Column 12, Line 14, amend "911" to "1011"
Column 12, Line 14, amend "902" to "1002"
Column 12, Line 15, amend "904" to "1004"

Signed and Sealed this
Twenty-second Day of May, 2018

Andrei Iancu
*Director of the United States Patent and Trademark Office*

CERTIFICATE OF CORRECTION (continued)
U.S. Pat. No. 9,460,886 B2

Column 12, Line 17, amend "911" to "1011"
Column 12, Line 17, amend "905" to "1005"
Column 12, Line 18, amend "904" to "1004"
Column 12, Line 23, amend "910" to "1010"
Column 12, Line 23, amend "912" to "1012"
Column 12, Line 24, amend "905" to "1005"
Column 12, Line 24, amend "913" to "1013"
Column 12, Line 25, amend "912" to "1012"
Column 12, Line 26, amend "914" to "1014"
Column 12, Line 28, amend "914" to "1014"
Column 12, Line 33, amend "914" to "1014"
Column 12, Line 35, amend "914" to "1014"
Column 12, Line 36, amend "915" to "1015"
Column 12, Line 40, amend "921, 922, and 923" to "1021, 1022, and 1023"
Column 12, Line 42, amend "901" to "1001"
Column 12, Line 45, amend "901" to "1001"
Column 15, Line 31, amend "increasing" to "decreasing"